United States Patent [19]

Murray

[11] Patent Number: 5,155,253
[45] Date of Patent: * Oct. 13, 1992

[54] TRANSVINYLATION PROCESS FOR THE PREPARATION OF THERMALLY LABILE VINYL COMPOUNDS AND FOR VINYL COMPOUNDS PREPARED FROM THERMALLY LABILE ACIDS

[75] Inventor: Rex E. Murray, Charleston, W. Va.

[73] Assignee: Union Carbide Chemicals & Plastics Technology Corporation, Danbury, Conn.

[*] Notice: The portion of the term of this patent subsequent to Jan. 1, 2008 has been disclaimed.

[21] Appl. No.: 676,443

[22] Filed: Mar. 28, 1991

Related U.S. Application Data

[60] Continuation-in-part of Ser. No. 592,661, Oct. 4, 1990, which is a division of Ser. No. 213,697, Jun. 30, 1988, Pat. No. 4,981,973.

[51] Int. Cl.$^5$ .......................................... C07C 67/343
[52] U.S. Cl. ........................................ 560/225; 560/1; 560/71; 560/104; 560/113; 560/189; 560/95; 560/201; 560/261; 568/685; 568/687
[58] Field of Search .................. 560/1, 71, 104, 113, 560/189, 95, 201, 261, 225; 568/685, 687

[56] References Cited

U.S. PATENT DOCUMENTS

| | | | |
|---|---|---|---|
| e. 27,663 | 6/1973 | Fernholtz et al. | 260/497 A |
| 2,245,131 | 9/1942 | Herrmann et al. | 260/476 |
| 2,299,862 | 10/1942 | Toussaint et al. | 260/410 |
| 2,989,554 | 6/1961 | Mayne et al. | 260/410.9 |
| 2,997,494 | 8/1961 | Brown | 260/410.9 |
| 3,000,918 | 9/1961 | Wilip et al. | 260/410.9 |
| 3,117,145 | 1/1964 | Ehrreich | 260/410.9 |
| 3,158,633 | 11/1964 | Port et al. | 260/410.9 |
| 3,179,641 | 4/1965 | Brown et al. | 260/87.1 |
| 3,188,319 | 6/1965 | Smidt et al. | 260/326 |
| 3,201,357 | 8/1965 | Fang et al. | 560/217 |
| 3,337,611 | 8/1967 | Beardon, Jr. | 260/491 |
| 3,391,130 | 7/1968 | Bolstad et al. | 260/89.1 |
| 3,454,644 | 7/1969 | Dewhirst | 260/570.9 |
| 3,560,534 | 2/1971 | MacDonald | 260/410.9 |
| 3,579,562 | 5/1971 | Weigert | 260/465.1 |
| 3,647,832 | 3/1972 | Chabardes et al. | 260/429 J |
| 3,725,305 | 4/1973 | Wilkinson | 252/429 R |
| 3,751,449 | 8/1973 | Gobran et al. | 260/486 R |
| 3,755,387 | 8/1973 | Young | 260/410.9 N |
| 3,786,102 | 1/1974 | Godfrey | 260/615 R |
| 3,793,355 | 2/1974 | Wilkinson | 260/429 R |
| 3,965,155 | 6/1976 | Smith et al. | 260/491 |
| 3,965,156 | 6/1976 | Smith et al. | 260/491 |
| 4,112,235 | 9/1978 | Schmerling | 560/1 |
| 4,175,056 | 11/1979 | Antos | 252/441 |
| 4,415,499 | 11/1983 | Blum et al. | 260/410.9 N |
| 4,424,359 | 1/1984 | Kaschig et al. | 560/255 |
| 4,446,073 | 5/1984 | Qualeatti et al. | 260/409 |
| 4,458,088 | 7/1984 | Hardman et al. | 560/217 |
| 4,640,302 | 2/1987 | Drent | 260/410.9 R |
| 4,647,691 | 3/1987 | Lin et al. | 560/175 |
| 4,658,053 | 4/1987 | Green | 560/234 |
| 4,664,851 | 5/1987 | Drent | 560/175 |
| 4,731,467 | 3/1988 | Drent et al. | 560/204 |
| 4,981,973 | 1/1991 | Murray | 548/229 |

FOREIGN PATENT DOCUMENTS

| | | |
|---|---|---|
| 1249847 | 9/1967 | Fed. Rep. of Germany ...... 560/175 |
| 827718 | 2/1960 | United Kingdom . |
| 877103 | 9/1961 | United Kingdom . |

OTHER PUBLICATIONS

Sandler, S. R., Journal of Chemical and Engineering Data, vol. 14, No. 4, Oct. 1966, pp. 503–506.
Slinckx, G. and Smets, G., Tetrahedron, vol. 22, 1966, pp. 3163–3171.
Hopff, H. and Osman, Maged A., Tetrahedron, vol. 24, 1968, pp. 3887–3890.
Adelman, R. L., Journal Organic Chemistry, 14, 1949, pp. 1057–1077.
Henry, P. M., Accounts of Chemical Research, vol. 6, 1973, pp. 16–24.
Sabel, A. et al., Chem. Ber. 102, 1969, pp. 2939–2950.
McKeon, J. E., et al. Tetrahedron, vol. 28, 1972, pp. 227–238.
Secemski, I. I. et al., Journal of the American Chemical Society, vol. 93, No. 14, 1971, pp. 3547–3550.
Henry, P. M., Journal of the American Chemical Society, vol. 93, No. 16 1971, pp. 3853–3859.
Henry, P. M., Journal of the American Chemical Society, vol. 94, No. 21, 1972, pp. 7311–7322.
Pandey, R. N. et al., Canadian Journal of Chemistry, vol. 53, 1975, pp. 2223–2231.
Allen, N. P. et al., Inorganica Chimica Acta, 28, 1978, pp. 231–235.
Rotem, M. et al., Organometallics, 2, 1983, pp. 1689–1691.
Mitsudo, T. et al., J. Org. Chem., vol. 50, No. 9, 1985, pp. 1566–1568.
Mitsudo, T. et al., J. Org. Chem., vol. 52, No. 11, 1987, pp. 2230–2239.

(List continued on next page.)

Primary Examiner—James H. Reamer
Attorney, Agent, or Firm—Sharon H. Hegedus

[57] ABSTRACT

A process for the transvinylation of a vinyl derivative of a Bronsted acid with a different Bronsted acid which comprises providing a liquid phase mixture containing said vinyl derivative and said Bronsted acid in the presence of a ruthenium compound at a temperature at which transvinylation occurs and recovering as a product of transvinylation the vinyl derivative of the different Bronsted acid. The process is most favorably employed using carboxylic acids to make vinyl esters of carboxylic acids.

54 Claims, No Drawings

OTHER PUBLICATIONS

Vinyl Polymers (Acetate), Kirk-Othmer Encyclopedia of Chemical Technology, Third Edition, vol. 23, pp. 817-847.

Crooks, G. R. et al., J. Chem. Soc. (A), 1969, pp. 2761-2766.

Cotton, F. A. et al., Chemical Communications, 1971, pp. 967-968.

Spencer, A. et al., J. C. S. Dalton, 1972, pp. 1570-1577.

Legzdins, P. et al., J. Chem. Soc. (A), 1970, pp. 3322-3326.

Gareev, G. A. et al., Zhurnal Organicheskoi Khimii, vol. 13, No. 3, 1977, pp. 606-607.

Robinson, S. D. et al., J. C. S. Dalton, 1973, pp. 1912-1920.

Fouda, S. A. et al., Inorganic Chemistry, vol. 17, No. 11, 1978, pp. 3213-3220.

Spencer, A., Inorg. Nucl. Chem. Letters, vol. 12, 1976, pp. 661-663.

Komiya, S. et al., Chemistry Letters, 1987, pp. 1287-1290.

TRANSVINYLATION PROCESS FOR THE PREPARATION OF THERMALLY LABILE VINYL COMPOUNDS AND FOR VINYL COMPOUNDS PREPARED FROM THERMALLY LABILE ACIDS

CROSS-REFERENCE TO RELATED APPLICATIONS

This application is a continuation-in-part of U.S. application Ser. No. 592,661, filed Oct. 4, 1990, which is a divisional of application Ser. No. 213,697, filed Jun. 30, 1988, now U.S. Pat. No. 4,981,973.

BRIEF DESCRIPTION OF THE INVENTION

There is described a process for the transvinylation of a vinyl derivative of a Bronsted acid with a different Bronsted acid which comprises providing a liquid phase a vinyl derivative of a Bronsted acid with a different Bronsted acid which comprises providing a liquid phase a vinyl derivative of a Bronsted acid with a different Bronsted acid which comprises providing a liquid phase mixture containing said vinyl derivative and said Bronsted acid in the presence of a ruthenium compound at a temperature at which transvinylation occurs and recovering as a product of transvinylation the vinyl derivative of the different Bronsted acid.

There is also described an improved process for the preparation of thermally labile vinyl compounds and for the preparation of vinyl compounds from thermally labile Bronsted acids which comprises reacting a vinyl derivative of a first Bronsted acid with a thermally labile Bronsted acid in the presence of a ruthernium compound at a temperature at which transvinylation occurs and recovering ad a product of transvinylation the vinyl derivative of the thermally labile acid. The vinyl product derivative itself may, or may not, be thermally labile depending on the vinyl derivative of the Bronsted acid.

BACKGROUND TO THE INVENTION

Transvinylation or vinyl interchange technology has existed for several decades. The reaction can be illustrated by the reaction of a vinyl ester or vinyl ether with an active hydrogen containing compound, as in the following:

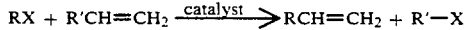

$$RX + R'CH=CH_2 \xrightarrow{catalyst} RCH=CH_2 + R'-X$$

wherein R is carboxy, amido, aroxy, alkoxy, and the like; X is hydrogen, hydroxyl, alkyl, aryl, and the like; and R' is carboxyl, amido, alkyl, substituted alkyl, aryl or substituted aryl.

Adlman, Journal Organic Chemistry, 14, po. 1057-1077, 1949, at p. 1057, termed transvinylation "ther 'Vinyl Interchange' Reaction, to differentiate it from typical ester interchange and ester-acid interchange reactions". . . Adelman noted the following advantages for this reaction:

"The very mild reaction conditions and the low yield of byproducts lead to high yields of monomers of greater purity and activity than those prepared by the reaction of acetylene with acids.

"Furthermore, vinyl esters of dibasic acids are prepared much mor easily by vinyl interchange than through the acetylene route, and recent work in this laboratory has shown that the reaction of vinyl acetate catalyzed with mercuric salts is not restricted to carboxylic acids, but will occur with other compounds containing active hydrogen, such as acetoacetic ester and glycolic esters."

McKeon, et al., *Tetrahedron*, 28, pp. 227-232 (1972) show the vinyl interchange reaction between a vinyl ether and an alcohol using a palladium catalyst. Other sources report the transvinylation reaction between vinyl chloride and a carboxlyic acid.

U.K. Patent No. 1,486,443 describes a transvinylation reaction for the production of a vinyl ester of an organic carboxylic acid by transvinylating a vinyl ester of an organic carboxylic acid with an organic carboxylic acid whose vinyl ester has a lower boiling point than the vinyl ester reactant. Because the boiling point of the vinyl ester reactant is higher than the boiling point of the vinyl ester product, it is stated that separation of the lower boiling point, more volatile product, from the higher boiling point, less volatile reactant, is facilitated as the reaction proceeds. Mercury, palladium and platinum based catalysts are disclosed, and the process is preferably carried out at low temperatures.

The literature suggests that the preferred catalysts for transvinylation reactions have been mercury and palladium based compounds. However, Pt(II) and Rh(III) have been reported by A. Sabel, J. Smidt, R. Jira and H. Prigge, *Chem. Ber.*, 102, pp. 2939-2950 (1969), to catalyze the reaction. In addition, Young, U.S. Pat. No. 3,755,387, patented Aug. 26, 1973, entitled: "A Vapor Phase Transvinylation Process", claims the use of supported Hg, Pd, Pt, Ir, Rh, Ru, or Os salt catalysts in a vapor phase transvinylation process. The experimental portion discloses the use of only palladium on carbon, copper on carbon, iron on carbon, palladium/copper on carbon, palladium/copper/iron on silica, mercuric acetate on carbon, and mercuric chloride on carbon. Hg. and Pd are cited, at col. 1, line 67, as the preferred metals. There is no recognition by this patentee of any special advantages to (i) the use of ruthenium compounds as catalysts for transvinylation reactions and (ii) effecting the reaction in a liquid phase reaction using a ruthenium compound as the catalyst.

Significant deficiencies in these prior art technologies are:

1. The mercury-based catalyst is toxic, undesirably volatile, and is typically activated with sulfuric acid to promote reaction and then deactivated by neutralization with base prior to product distillation. Traces of adventitious free acid generated by this sytem tend to promote ethylidene diester formation.
2. Palladium-based catalysts are not sufficiently thermally stable to allow product removal by distillation at elevated temperatures; the catalyst often deactivates forming metallic Pd.

M. Roten, et al., *Organometallics*, 2, pp. 1689-1691 (1983), T. Mitsudo, et al., *J. Org. Chem.*, 50, pp. 1566-1568 (1985), and T. Mitsudo, et al., *J. Org. Chem.*, 52, pp. 2230-2239 (1987) shows the use of ruthenium based catalysts to promote the addition of carboxlyic acids to alkynes and producing alkenyl carboxylates. In particular, the reaction of carboxylic acids with substituted alkynes is facile. The reaction of carboxylic acids with acetylene (vinylation) to give vinyl esters is also possible, but at a much slower rate. Various catalyst precursors have been stidued which include ruthernium carbonyl, bis(eta 5-cyclooctadienyl)ruthenium (II)/trin-butylphosphine, and bis(eta 5-cyclooctadienyl)ruthenium (II)/trialkyl-phosphine/maleic anhydride.

The use of these and similar ruthenium compositions as transvinylation catalysts has apparently not been recognized until this invention. The beneficial use of ruthenium-containing compounds as catalysts for transvinylation processes which overcome several of the deficiencies noted for the prior art catalysts has not been appreciated until this invention. The beneficial use of ruthenium compounds as catalysts for transvinylation processes for the preparation of vinyl compounds from thermally labile acids and for the preparation of thermally labile vinyl compounds and the improvement that can be achieved in such processes due, in part, to the use of such ruthenium compounds had not been realized before this invention.

There is a need in the transvinylation art for a catalyst having high catalytic activity at convenient elevated temperatures which would allow the facile removal of the desired product of the reaction without interfering with other components present in the reaction product mixture. There is also a need in the transvinylation art for a transvinylation process by which thermally labile vinyl compounds may be beneficially prepared economically and in which a thermally labile Bronsted acid may be used readily without isomerization, polymerization, decarboxylation, acylation or the like. There is a further need in the transvinylation art for a transvinylation process in which only one Bronsted acid functional grup in molecules which contain more than one such functional group can be selectively transvinylated.

THE INVENTION

The invention relates to a process for the transvinylation of a vinyl derivative of a Bronsted acid with a different Bronsted acid which comprises providing a liquid phase mixture containing said vinyl derivative and said Bronsted acid in the presence of a ruthenium compound at a temperature at which transvinylation occurs and recovering as a product of transvinylation the vinyl derivative of the different Bronsted acid. In the preferred practice of the process, the ruthenium is soluble in the reaction mixture in a catalytically effective amount.

In another aspect of the invention, there is provided a process for the preparation of a vinyl derivative of a thermally labile Bronsted acid by transvinylation reaction of a vinyl derivative of a Bronsted acid with a thermally labile Bronsted acid in the presence of a ruthenium compound capable of catalyzing the reaction. In accordance with this aspect of the invention, the vinyl derivative of the Bronsed acid has a boiling point in the range of from about equal to, to slightly less than the boiling point of the thermally labile Bronsted acid to greater than the boiling point of the thermally labile Bronsted acid, and greater than the boiling point of the vinyl derivative of the thermally labile Bronsted acid. The vinyl derivative of the thermally labile Bronsted acid is removed from the reactor as the reaction progresses. Preferably the vinyl derivative of the thermally labile Bronsted acid is removed continuously as the reaction proceeds. In carrying out the process, the thermally labile Bronsted acid is fed to the reaction at a rate to maintain the concentration of the theramlly labile Bronsted acid in the reactor during the transvinylation reaction at less than about 40 mole % in order to minimize isomerization, polymerization, decarboxylation, acylation or the like to levels which are not detrimental.

Where the vinyl derivative of the thermally liable Bronsted acid is likewise thermally labile, the combiend concentration of thermally labile Bronsted acid and the vinyl derivative thereof in the reactor is maintained below about 40 mole %.

The present invention also provides a process for the selective transvinylation of a single Bronsted acid functional group in molecules which contain more than one such functional group.

DETAILES OF THE INVENTION

Transvinylations are equlibrium reactions which typically have an equilibrium constant of about 1. The efficiency of the reaction is measured by the extent the desired transvinylation reaction product is present in the equilibrium reaction products. In other words, the reaction generates more than one product and the effectiveness of the process is frequently measured by the proportion of the desired product to the other products of the transvinylation reaction.

The reaction of the invention involves the combination of

---
a vinyl derivative of a Bronsted acid;
a different Bronsted acid with which to interchange;
a ruthenium compound; and
liquid phase reaction conditions.
---

The vinyl derivative is any compound in which there is a vinyl group bonded to a Bronsted acid. They may be characterized as vinylated Bronsted acids. Vinyl embraces groups of the formula $R^0R^1C=CH-$ wherein $R^0$ and $R^1$ are each individually one of hydrogen, alkyl of 1 to about 12 carbona toms, cycloalkyl, aryl, alkyl ethers, and the like. The Bronsted acid is any species which can act as a source of protons.

Illustrative of suitable vinyl derivatives of a Bronsted acid for the practice of the invention, are vinyl acetate, vinyl pivalate, vinyl benzoate, vinyl methacrylate, vinyl acrylate, divinyl isophthalate, divinyl terephthalate, divinyl adipate, vinyl propionate, vinyl stearate, vinyl salicylate, vinyl cinnamate, vinyl 2-ethylhexanoate, vinyl cyclohexanoate, N-vinyl pyrrolidinone, N-vinylsuccinimide, vinyl phenyl ether, vinyl methyl ether, vinyl ethyl ether, N-vinyl 2-oxazolidinone, N-vinyl ethyleneurea, N-vinyl N-acetylethyleurea, 2-vinyloxyethyl acetate, 2-vinyloxyethyl pivalate, 2-vinyloxyethylacrylate, vinyl chloride, vinyl sulfonamides, and the like.

Preferred vinyl derivatives are the vinyl esters of carboxylic acids and the vinyl alkyl or aryl ethers, mainly because they are more commercially available.

Illustrative of suitable Bronsted acids for the practice of the invention are carboxylic acids such as monocarboxylic and polycarboxylic acids illustrated by acetic acid, propionic acid, butyric acid, pivalic acid and other neo acids, stearic acid, and other vinyl esters of fatty acids, benzoic acid, terephthalic acid, isophthalic acid, phthalic acid, adipic acid, succinic acid, malic acid, maleic acid, polyacrylic acids, crotonic acid, acrylic acid, methacrylic acid, salicyclic acid, cinnamic acid, 2-ethylhexanoic, and cyclohexanoic acid; amides such as 2-pyrrolidinone, 2-pyrrolidone, ε-caprolactam, 2-oxazolidinone, ethyleneurea, N-acetyl ethyleurea, and succinimide; alcohols such as methanol, ethanol, n-propanol, isobutanol, fluorinated alkanols such as 1,1,1,3,3,3-hexafluoro-2-propanol, monoethanolamine, diethanolamine, and triethanolamine; phenolic compounds such as phenol, resorcinol, and Bisphenol A [2,2-bis(4-hydroxyphenyl)propane]; amino compounds which are sufficiently acidic such as secondary aromatic amines, azoles, blocked amines and imines, silazanes and the like; hydroxy esters such as hydroxalkyl acrylates (viz., 2-hydroxyethyl acrylate, 2-hydroxyethyl methacrylate) and hydroxyalkyl alkanoates (viz., 2-hydroxyethyl acetate, 2-hydroxyethyl pivalate); sulfonamides such as diethyl sulfonamide and toluene sulfanamide; silanols such as phenyl silane triol, diphenyl silane diol, triphenyl silane mono-ol, dimethyl silane diol, trimethylsilane mono-ol, and the like.

The preferred Bronsted acids are the carboxylic acids, the alcohols, the imines, the amides, the imides, the phenolics, and the like.

Illustrative of transvinylation reactions that may be carried out by the process of the invention, are the following:

| Vinyl Derivative | Bronsted Acid | Product |
| --- | --- | --- |
| vinyl acetate | + pivalic acid | → vinyl pivalate |
| vinyl benzoate | + pivalic acid | → vinyl pivalate |
| vinyl acetate | + methacrylic acid | → vinyl methacrylate |
| vinyl acetate | + acrylic acid | → vinyl acrylate |
| vinyl acetate | + isophthalic acid | → divinyl isophthalate |
| vinyl acetate | + terephthalic acid | → divinyl terephthalate |
| vinyl propionate | + adipic acid | → divinyl adipate |
| vinyl acetate | + benzoic acid | → vinyl benzoate |
| vinyl acetate | + propionic acid | → vinyl propionate |
| vinyl pivalate | + stearic acid | → vinyl stearate |
| vinyl acetate | + salicyclic acid | → vinyl salicylate |
| vinyl acetate | + cinnamic acid | → vinyl cinnamate |
| vinyl propionate | + 2-ethylhexanoic acid | → vinyl 2-ethylhexanoate |
| vinyl acetate | + cyclohexanoic acid | → vinyl cyclohexanoate |
| vinyl acetate | + 2-pyrrolidinone | → N-vinyl 2-pyrrolidinone |
| vinyl pivalate | + 2-pyrrolidinone | → N-vinyl 2-pyrrolidinone |
| vinyl pivalate | + succinimide | → N-vinyl succinimide |
| vinyl methyl ether | + phenol | → vinyl phenyl ether |
| vinyl chloride | + methanol | → vinyl methyl ether |
| vinyl methyl ether | + ethanol | → vinyl ethyl ether |
| vinyl acetate | + 2-oxazolidinone | → N-vinyl 2-oxazolidinone |
| vinyl acetate | + ethyleneurea | → N-vinyl ethyleneurea |
| vinyl acetate | + N-acetyl ethyleneurea | → N-vinyl N-acetylethyleneurea |
| vinyl acetate | + 2-hydroxyethyl acetate | → 2-vinyloxyethyl acetate |
| vinyl pivalate | + 2-hydroxyethyl pivalate | → 2-vinyloxyethyl pivalate |
| vinyl pivalate | + 2-hydroxyethyl-acrylate | → 2-vinylhydroxyethyl acrylate |

In a more specific aspect of the invention, the different (second) Bronsted acid is thermally labile. Thermally labile as used herein means that the acid includes at least one moiety which will render the acid susceptible to isomerization, polymerization, decarboxylation or acylation under the thermal conditions at which the transvinylation reaction is conducted.

Thermally labile Bronsted acids embrace hydroxyl derivatives of benzoic acid including, for example, salicyclic acid, and acids of the formula:

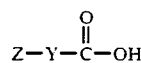

wherein Z is

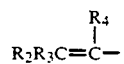

and $R_2$, $R_3$ and $R_4$ are each individually one of hydrogen, alkyl, aryl, halo, cyano, carbonyl, keto or carboxylate and Y is $(CH_2)_n$, aryl or substituted aryl. Where Y is $(CH_2)_n$, n is zero or one. In accordance with the invention, the thermally labile Bronsted acid has a lower boiling point than the vinyl derivative of the Bronsted acid, which is the reactant ester. The relativity of boiling points of these two reactants is important in order to ensure that the product ester, i.e., the vinyl derivative of the thermally labile Bronsted acid, can be removed from the transvinylation reactor as the transvinylation reaction proceeds, if desired.

Illustrative of thermally labile Bronsted acids for the practice of the invention are acrylic acid, methacrylic aic,d α-cyanoacrylic acid, chloroacrylic acid, fluoroacrylic acid, bromoacrylic acid, salicylic acid and acetoacetic acid. Preferred acids are acrylic acid and methacrylic acid because of the multitude of potential end uses for vinyl derivatives for those monomers.

Vinyl derivatives of Bronsted acids suitable for the practice of the invention for making vinyl derivatives of thermally labile Bronsted acids are vinyl esters that have at least about the same volatility as the thermally labile Bronsted acid. Suitable vinyl derivatives of Bronsted acids may thus have boiling points about equal to or even slightly less (about 10° C.) than the boiling point of the thermally labile acids. In that event, the vinyl derivative of the Bronsted acid can be recycled for use in the transvinylation reaction. Desirably the vinyl derivative of the Bronsted acidhas a boiling point greater than the boiling point of the thermally labile acid. Preferably vinyl derivatives of the Bronsted acids for use in the practice of the invention have a boiling point at least about 20° C. higher than the boiling point of the thermally labile Bronsted acid, and more preferably at least about 50° C. higher. Generally, the greater the difference in volatility between the heavy vinyl ester and the thermally labile acid, the greater the difference in volatility between the heavy vinyl ester and the vinyl derivative of the thermally labile acid reaction product. It is desirable that the difference in volatility between the heavy vinyl ester and the vinyl reaction product be sufficient to allow the transvinylation reaction to be conducted in a manner such that the vinyl reaction product can be separated easily from the transvinylation reactor as the transvinylation reaction progresses. In addition, removal of the vinyl reaction product from minor or trace amounts of heavy vinyl reactant ester by post reaction refining processes is facilitated.

Vinyl derivatives of Bronsted acids suitable for making vinyl derivatives of thermally labile acids are vinyl esters of carboxylic acids, including polymers which contain vinyl derivatives of carboxylic acids. Suitable vinyl derivatives desirably have at least seven carbon atoms. Examples of suitable vinyl derivatives are vinyl pivalate, vinyl vlaerate, vinyl neodecanoate, vinyl 2-ethylhexanoate, vinyl neononanoate, vinyl benzoate, vinyl heptanoate, vinyl laurate, vinyl palmitate, vinyl stearate, vinyl versatate and the like.

Use of the process of the present invention to make vinyl acrylate and vinyl methacrylate by the transvinylation of a heavy vinyl derivative with acrylic acid and methacrylic acid, respectively, has overcome serious polymerization problems that were encountered in the separation of vinyl acrylate or vinyl methacrylate from the transvinylation mixture when vinyl acetate is used as the transvinylation agent. Use of the heavy vinyl derivative feedstock, maintaining a very low combined acrylic acid and vinyl acrylate concentration in the reactor and driving the equilibrium reaction toward the formation of the vinyl derivative of the thermally labile Bronsted acid through continuous removal of the vinyl acrylate or vinyl methacrylate product makes detrimental levels of polymerization preventable. Further, refining is greatly facilitated.

The process of this invention provides an excellent route to many hard to produce vinyl compounds because of the desirable physical and chemical properties of the ruthenium compounds which provide the basis for the catalytic reaction. The ruthenium catalysts are easily obtainable as soluble components and can be used in the form of non-volatile compounds possessing high tehrmal stability, and exhibiting high catalytic activity only at elevated temperatures. Unlike palladium, the ruthenium-based catalyst does not lead to observable metal precipitation, even when reaction is conducted at temperatures above 150° C. From a practical standpoint, the physical and chemical properties of the ruthenium catalyst (soluble, non-volatile, and possessing high thermal stability) permit product removal by distillation. These properties suggest that the ruthenium catalyst system is far superior to prior art transvinylation technologies using palladium and mercury.

The selection of a suitable ruthenium compound to provide the catalytic activity for the transvinylation reaction is not narrowly critical. Essentially any ruthenium compound can be effectively employed to carry out the transvinylation reaction. However, the invention is believed to involve novel ruthenium-based catalysts which promote the vinyl interchange (transvinylation) between vinyl derivatives and the Bronsted acids. It is believed the primary requirement for the generation of such catalysts and the requisite catalytic activity are ruthenium precursors to the catalyst which can be converted to $[Ru(CO)_2RCO_2]_n$ or similar compounds even if the precursor during the reaction fails to be converted to such structures. $[Ru(CO)_2RCO_2]_n$ or similar compounds may or may not be the transvinylation catalyst of the invention but it has been noted that the use of such compounds assures the effective catalytic reaction and the results herein characterized. The process of this invention may be practiced with a vast array of ruthenium compounds. Even instances where the ruthenium compound is too stable for catalyzing the reaction, catalysis can be effected by including a compound which does not adversely affect the transvinylation reaction and stimulates the ruthenium compound to be converted to a species having catalytic activity. For example, ruthenium chloride is a sluggish catalyst but is made quite active by the addition of an alkali such as an alkali metal salt of a carboxylic acid, viz. sodium acetate. It is not presumed that simple ruthenium salt compounds are the catalyst or that many of the ruthenium compounds herein used to effect the catalytic reaction are the catalyst. The exact ruthenium containing compound or compounds that constitute the catalyst of this invention is not appreciated but what is appreciated is that many ruthenium compounds can be used to in situ generate the catalyst. The diversity of the selection of ruthenium compounds suitably employable as precursors to catalysts in the process of the invention is quite broad; illustrative of this point—the precursor compounds may range from supported ruthenium such as ruthenium on carbon, alumina, and the like, to ruthenium carbonyl to bis(eta 5-cyclooctadienyl)ruthenium-(II)/tri-n-butylphosphine and to bis(eta 5-cyclooctadienyl)-ruthenium(II)/trialkyl-phosphine/- maleic anhdride.

The most preferred catalysts are formed from ruthenium carbonyl carboxylates, or precursors which can convert into these species. Based on an analysis of the literature, certain assumptions of the likely structure of the catalyst have been made. Based on the recognition that ruthenium carbonyl reacts with carboxylic acids to product soluble orange-yellow complexes possessing the empirical formula $[Ru(CO)_2RCO_2]_n$ and the fact these complexes appear sufficiently labile to accommodate coordination of vinyl acetate and subsequently catalyze exchanges between vinyl-bound and ruthenium-bound carboxylates, it is belived that such structures are involved in the catalysis of the transvinylation process. For example, it is known that in the presence of carbon monoxide, $[Ru(CO)_2RCO_2]_n$ is readily converted to $Ru_2(CO)_6(RCO_2)_2$ dimer. Analogously, substitution with other ligands such as phosphines gives $Ru_2(CO)_4(L)_2(RCO_2)_2$ complexes. Similar affinity for coordination is thus proposed for vinyl esters. The addition of one equivalent of triphenylphosphine (per ruthenium) to a ruthenium carbonyl-based catalyst reduced transvinylation rate by a factor of about ten, indicating the presumably formed complex, $Ru_2(CO)_4(L)_2(RCO_2)_2$ is a less active precursor. Similarly, the addition of one equivalent of the phosphonium ylide, 2-(triphenylphosphor-anylidine) succinic anhydride, resulted in erduced reaction rates. The complex, hydrido(acetato)tris(triphenylphosphine)ruthenium(II), exhibited meager activity, indicating that higher phosphorus to ruthenium ratios lead to a more serious rate inhibition. Tetrahydridotetraruthenium dodecacarbonyl, $H_4Ru_4(CO)_{12}$, can also be used to form the catalyst. Ruthenium(III) chloride, ruthenium(III) iodide, tris(2,2-bipyridyl)ruthenium(II) chloride hexahydrate, and ruthenocene exhibited only very slight catalytic activity, which further substantiates that the level of catalyst activity intimately depends upon the form of the ruthenium precursor.

It has been found that the presumed catalyst precursor, $[Ru(CO)_2RCO_2]_n$, can be generated in several ways. For example, the trinuclear complex, $[Ru_3O(OAc)_6(H_2O)_3]OAc$, gives an efficient transvinylation catalyst. Infrared analysis indicates that $[Ru_3O(OAc)_6(H_2O)_3]OAc$ can convert to $[Ru(CO)_2RCO_2]_n$ under transvinylation reaction conditions. This is even observed when the reaction is conducted under nitrogen atmosphere, rather than carbon monoxide. Frequently, there is sufficient adventitious carbon monoxide available to in situ convert all of the Ru to a carbonyl form.

As was previously stated, ruthenium trihalide-based precursors, e.g., ruthenium(III) chloride and ruthenium(III) iodide, exhibit only slightly activity. However, a very active and more selective catalyst can be generated in situ from ruthenium chloride and sodium acetate. This presumably produces the [Ru$_3$O(OAc)$_6$(H$_2$O)$_3$]OAc precursor and insoluble sodium chloride salt. The conditiosn useful for effective catalyst generation includes a ruthenium carboxylate precursor or a mixture of reagents which can generate a ruthenium carboxylate precursor. Dichlorotricarbonylruthenium-(II) dimer, [RuCl$_2$(CO)$_3$]$_2$, also gives an active, but non-selective catalyst which produces significant quantities of heavier by-products, tentatively believed to be ethylidine- and glycol-diesters. It is postulated that upon conversion to catalyst, [RuCl$_2$(CO)$_3$]$_2$ also forms traces of hydrochloric acid which are principally responsibel for the by-product formation. There is some very good evidence to substantiate these assumptions. Under similar reaction condntions, but in the absence of ruthenium, hydrochloric acid has been shown to readily promote heavy by-product formation. The salient conclusion is that ruthenium halide precursors can be used in the invention, however they are best used in conjunction with alkali metal carboxylates (typically sodium acetate) to facilitate precipitation of the alkali metal halide (typically sodium chloride). Non-carbonyl and non-carboxylate containing ruthenium compounds can also lead to highly active catalyst. In experiments conducted under carbon monoxide atmosphere, ruthenium-(III) acetyl-acetonate, ruthenium(IV) oxide, ruthenium on carbon, and ruthenium on alumina have all shown catalytic activity. Under these conditions, ruthenium powder shows trace activity. A route to transvinylation catalysts from ruthenium halides involves, as pointed above, displacing the halide from the ruthenium precursor. It is also likely that other metal salts, known to precipitate halides (Ag$^+$, Cu$^+$, Hg$^+$) would also be effective in combination with ruthenium halides to provide the catalyst precursor.

The amount of the ruthenium catalyst useful for effecting the transvinylation reaction is not narrowly critical. The typical amount is a catalytically effective amount, that is, an amount which is sufficient to effect the desired vinyl interchange. For example, it has been established that ruthenium catalyst concentrations ranging roughly from about 30,000 parts to about 0.5 part per million (ppm) ruthenium based on the weight of the liquid phase reaction medium can be used to effect the reaction. It is believed that larger and smaller amounts of the catalyst may be used to effect the reaction. The most preferred range is from about 0.1 ppm to about 500 ppm ruthenium, same basis.

In the practice of the invention to prepare vinyl derivatives of thermally labile Bronsted acids it is desirable to maintain an adequate ruthenium concentration to promote a rapid transvinylation rate. The benefits of a rapid transvinylation rate are manifested in a reduction in the polymerization or degradation of the thermally labile Bronsted acid due, at least in part, to the shorter residence time of the thermally labile Bronsted acid in the reactor. Catalyst concentrations in the range of from about 0.1 ppm to about 5000 ppm ruthenium relative to the total charged reactants and solvents in the reactor are suitable. Catalyst concentrations in the range of from about 500 ppm to about 5000 ppm (same basis) have been found to provide reasonable selectivities and reasonable transvinylation rates. It will be appreciated that the catalyst concentration can be optimized depending on the vinyl derivative of the thermally labile Bronsted acid to be made, reaction temperature, and the like.

It has also been found that pretreatment or conditioning of the catalyst may enhance the transvinylation reaction by preventing polymerization, for example. By way of illustration, in the preparation of vinyl acrylate by the transvinylation of a heavy vinyl ester with acrylic acid, it has been found that treating the catalyst with a small amount of acrylic acid at about 110° C. for 0.5-1 hour prior to transvinylation prevents detrimental levels of polymerization.

It is desirable that the transvinylation reaction be carried out in the absence of an amount of water in the reaction mixture that inhibits the production of the desired vinyl interchanged product. However, as shown in the Examples 60-63 below, the reaction can be carried out in the presence of significant quantities of water. The inhibiting effects of water are reactant dependent. Increasing the concentration of ruthenium catalyst in the reaction mixture is a facile method of overcoming water inhibition in many cases, if not most cases. It has been noted that there is a correlation between the amount of ruthenium catalyst employed and the amount of water usable in the process. The more ruthenium present, the more water that may be present in the reaction without adversely affecting the reaction. It is desirable to use a system which is substantially water-free. As a rule, the amount of water present in the reaction is desirably less than about 25 weight % of the weight of the reaction mixture. Preferably, the amount of water in the reaction is less than about 15 weight % of the weight of the mixture. The smaller the amount of water present the better the reaction operates and greater the yield of desired reaction product. Essentially anhydrous reaction systems as herein characterized are preferred. For example, it is more desirable that the amount of water in the reaction be less than about 10 weight % of the weight of the mixture. Preferably, the amount of water in the reaction is less than about 5 weight % of the weight of the mixture, more preferably less than about 2.5 weight % of the weight of the mixture, most preferably less than about 1 weight % of the weight of the mixture. Water concentration in the reaction mixture can be controlled by conventional procedures, such as by drying the reactants carefully, azeotropically distilling the water from the reaction when an azeotrope is formed, and by the addition of molecular sieve drying agent.

The temperature at which the reaction can be carried out is also not narrowly critical. The reaction rate varies with the identity of the Bronsted acid to be transvinylated. The more acidic acids tend to be reactive at lower temperatures. It is also desirable to operate at a temperature at which the acid reactant is dissolved or liquid. The process is favorably effected by keeping the reaction temperature below the boiling point of the highest boiling reactant or at sufficient pressure to maintain the liquid state. When feasible, the liquid phase condition can best be accomplished by operating at temperatures above the melting point of the acide. Nonetheless, terephthalic acid (mp > 300° C.), which is insoluble in most catalyst-compatible solvents, was transvinylated to divinyl terephthalate by conducting the reaction in aromatic ester solvents at elevated temperatures (ca. 150° C.). These conditions presumably facilitate transvinylation by achieving slight solubility of the terephthalic acid. Overall, the temperature at which the reactions may be carried out range from about 20° C. to about 300° C., but about 50° C. to about 200° C. is more preferred.

The optimum reaction conditions depend chiefly on the Bronsted acid (such as a carboxylic acid) to be transvinylated. If the acid is soluble at the reaction temperature, it is better to operate without solvent. It is also preferred, when feasible, to conduct the reaction at temperatures above the melting point of the acid.

In the preparation of vinyl derivatives of thermally labile Bronsted acids, the reaction temperature is dependent upon the lability of both the reactant acid and the vinyl derivative product. Higher reaction temperatures are preferred to increase the transvinylation reaction rate. Reaction rate varies with the identity of the thermally labile acid to be transvinylated and its solubility in the reaction medium, as it is generally desirable to transvinylate at a temperature at which the acid is dissolved in the reaction medium. Accordingly, it is generally desirable to transvinylate at temperatures above the melting point of the acid when feasible, although a non-polar solvent can be used if necessary. Generally, the temperature for the transvinylation reaction is in the range of from about 75° C. to about 200° C., and preferably it is in the range of about 80° C. to about 160° C. More preferably, the temperature for the transvinylation reaction is in the range of about 110° C. to about 140° C. It will be appreciated that reaction side products such as anhdride formation tend to increase at higher transvinylation temperatures, especially in the absence of an inert atmosphere such as carbon monoxide. However, in the presence of an inert atmosphere, particularly carbon monoxide, higher reaction temperature is acceptable.

Transvinylation works best without solvents or in non-polar solvents. Suitable results have been achieved in solvents such as toluene, heptane, silicone oil, mineral oil, phenyl ether, phenylbenzoate, methyl benzoate, dimethylterephthalate, and dioctylphthalate. More highly polar solvents such as alcohols, water, sulfolane, Carbowaxes ®, and N-methylpyrolidinone tend to inhibit reaction rates. Oxygenated aromatics such as diphenylether, methylbenzoate, dimethylterephthalate, and dioctylphthalate are desirable solvents in the synthesis of divinylterephthalate and divinylisophthalate.

The invention is operational over a broad range of mole ratios of Bronsted acid (such as carboxylic acid) to vinyl derivative. The preferred ratio depends mostly on the transformation sought. In general, ratios of about 100/1 to about 1/100 are preferred and ratios of about 1/10 to about 10/1 are most preferred.

The mole ratio of the Bronsted acid (viz., carboxylic acid or carboxylate) to ruthenium should be at least 0.5 to 1. For the preparation of a vinyl derivative of a thermally labile Bronsted acid, the mole ratio is at least 1:1. Typically a higher concentration of acid is used in order to assure rapid conversion of the thermally labile substrate. The ruthenium concentration in the reaction mixture is a catalytically effective amount and this is typically in the parts per million range while the acid is typically a major component of the reaction mixture. Most preferably the mole ratio of the Bronsted acid to ruthenium is about 50/1 to about 1,000,000/1.

For the preparation of a vinyl derivative of a thermally labile Bronsted acid, it is preferred to continuously feed the thermally labile acid to the reaction medium under conditions in which the concentration of the thermally labile acid remains low in the reactor, that is, on the order of about 1 mole % to about 40 mole %, and, preferably from about 5 mole % to about 25 mole %, in order to minimize detrimental polymerization, isomerization, decarboxylation, or acylation of the acid in the reactor. Where the vinyl product ester, i.e., the vinyl derivative of the thermally labile acid, is removed as the thermally labile acid is reacted, the thermally labile acid is fed to the reactor at about the same rate as the rate at which the vinyl product ester is removed from the reactor. If the vinyl product ester is also thermally labile, then it is preferred to continously remove the vinyl product ester from the reactor as the transvinylation proceeds and to feed the thermally labile acid and remove the vinyl product ester at a rate such that the combined concentration of thermally labile acid and thermally labile vinyl product ester does not exceed about 40 mole % and preferably does not exceed about 20 mole %.

The residence time of the thermally labile Bronsted acid in the reactor is desirably as short as is possible in order to minimize polymerization or degradation of the acid. It is likewise desirable to minimize the residence time of the vinyl derivative of the thermally labile acid, especially where the vinyl derivative is also thermally labile. The residence time may vary greatly depending on the lability of the acid and the vinyl derivative, the reaction temperature and the ruthenium concentration. The more labile these components are, the shorter the residence time should be. Thus, the residence time may be a matter of several seconds, several minutes or even several hours.

Several reaction atmospheres, such as carbon monoxide, air, nitrogen, and ethylene, are compatible with the transvinylation catalyst. Nitrogen and ethylene are suitable in most situations. Carbon monoxide appears to improve catalyst selectivity. Air has been employed in conjunction with phenothiazine (polymerization inhibitor) for the synthesis of vinyl acrylates. In some instances the catalytic reaction produces small amounts of methane, carbon monoxide, and carbon dioxide by-products which obviously augment the initially charged reaction atmosphere. The reaction may be carried out at pressures which are subatmospheric, atmospheric or superatmospheric. In some situations, reaction can also be conducted under vacuu, such as in a distillation apparatus. A desirable reaction pressure is from about $10^{-6}$ torr to about 5,000 psia. The more desirable reaction pressure is from about $10^{-5}$ torr to about 800 psia. The preferred reaction pressure is from about $10^{-4}$ torr to about 550 psia. The preferred reaction pressure is superatmopsheric pressure, typically from about 16 to about 5,000 pounds per square inch absolute. The preferred reaction pressure for the preparation of a vinyl derivative of a thermally labile Bronsted acid is from about 0.01 mm Hg to about 1000 psia. The most preferred carbon monoxide partial pressure is from about 1 mm Hg to about 100 psia.

As pointed out previously the reaction is carried out under conditions at which all of the reactants are in the liquid phase. This does not require that the reaction environment be wholly in the liquid phase. It simply means that sufficient of the reactants and the catalyst be in the liquid phase that the reaction can occur in the liquid phase. For example, solid ruthenium on a solid support can be used as a catalyst precursor. In the presence of reactant, solvent and/or carbon monoxide, sufficient ruthenium can be converted to a liquid soluble compound such that the catalystic reaction is attainable.

A favorable aspect of the process of the invention is to shift the equilibrium of the reaction in the direction of the favored product so that higher concentrations of the product can be obtained based on the amount of starting materials employed. This can be done by the continuous removal of one of the products of the reaction so as to shift the equilibrium in a favorable direction without adversely affecting the catalyst and/or the ruthenium values. For the preparation of vinyl derivatives of thermally labile acids, it is preferred to continously remove the vinyl derivative to drive the reaction toward the production of the vinyl derivative and to minimize the residence time of the thermally labile acid in the reactor. Continuous removal of the vinyl derivative where the vinyl derivative is also thermally labile is also beneficial because it minimizes polymerization and/or degradation of the vinyl derivative in the reactor. The process is thus facilitated and yield is improved.

EXAMPLE 1

To a Fischer-Porter bottle were charged ruthenium carbonyl (0.316 grams), benzoic acid (183 gram, 1.50 moles), and vinyl acetate (258 grams, 3.00 moles). The bottle was attached to the reaction apparatus, purged and pressurized to 25 psig with carbon monoxide, and heated to 150° C. for 3 hours. The reaction mixture was cooled to ambient temperature, transferred to a 1 liter flask, and distilled by rotary evaporation under reduced pressure. The fraction taken at approximately 15; torr and 84° C. (187.8 grams) was redistilled through a 15 cm Vigreux column. Vinyl benzoate (100.4 grams, >99% pure by gc) was collected in fractions boiling from 90°-101° C. at 15 torr.

EXAMPLE 2

To a Fischer-Porter bottle were charged tris(aquo)-hexa-λ-aceto-λ$_3$-oxo-triruthenium acetate (0.032 grams), 2-ethylhexanoic acid (42.37 grams, 0.294 moles), and vinyl acetate (25.3 grams, 0.294 moles). The bottle was attached to the reaction apparatus, purged and pressurized to 25 psig with carbon monoxide, and heated to 150° C. for 3 hours. The reaction mixture was stripped of volatiles by rotary evaporation and the residue was distilled through a 15 cm Vigreux column. A fraction collected at 49° C./5 torr was vinyl 2- ethylhexanoate (9.0 grams, >99% pure by gc).

EXAMPLE 3

To a Fischer-Porter bottle were charged ruthenium carbonyl (0.118 grams), pivalic acid (68.43 grams, 0.67 moles), and vinyl benzoate (48.87 grams, 0.33 moles). The bottle was attached to the reaction apparatus, purged and pressurized to 25 psig with carbon monoxide, and heated to 150° C. for 2 hours. The cooled reaction mixture was charged to a 250 ml flask and vacuum distilled through a 15 cm Vigreux column. A fraction collected at 60.5°-65° C./150 torr (31.7 grams) was redistilled at atmospheric pressure (bp=114° C., 24.2 grams). It comprised vinyl pivalate.

EXAMPLE 4

To a Fischer-Porter bottle were charged ruthenium carbonyl (0.211 grams), adipic acid (7.3 grams, 0.05 moles), and vinyl acetate (21.5 grams, 0.25 moles). The bottle was attached to the reaction apparatus, purged and pressurized to 25 psig with nitrogen, and heated to 130° C. for 4.5 hours. The reaction mixture was stripped of volatiles by rotary evaporation and the residue was distilled through a 15 cm Vigreux column. A fraction collected at 72°-79° C./0.75 torr was divinyl adipate (1.5 grams, >98% pure by gc).

EXAMPLE 5

To a Fischer-Porter bottle were charged tris(aquo)-hexa-λ-aceto-λ-3-oxo-triruthenium acetate (0.9 1 grams), dioctylphthalate (150 grams), terephthalic acid (75 grams, 0.45 moles), and vinyl acetate (150 grams, 1.74 moles). The bottle was attached to the reaction apparatus, purged and pressurized to 25 psig with carbon monoxide, and heated to 175° C., for 4.5 hours. The reaction mixture was stripped of volatiles by rotary evaporation. Distillation through a short path column afforded a fraction boiling at 111° C./0.7 torr which solidified upon condensing (mp=76.5°-70.5° C.). It contained divinyl terephthalate.

EXAMPLE 6

Using a procedure similar to that of Example 5, isophthalic acid (75 grams) was converted to divinyl isophthalate at successive reaction temperatures of 150° C. for 3.5 hours and 175° C. for 2.25 hours. Distillation through a short path column afforded a fraction boiling at 117°-145° C./1.2 torr (7.1 grams) which solidified upon condensing (mp.=53.5°-56.5° C.). It comprised divinyl isophthalate.

EXAMPLES 7-12

The following examples in the followint table show a number of ruthenium catalyzed transvinylations conducted between vinyl acetate and a variety of carboxylic acids in which the vinyl ester products, in lieu of isolation, were characterized by either GC/Ir/Mass Spec or by GC retention time comapred with an authentic sample. The table lists the reaction conditions.

| Ex. No. | Carboxylic Acid | Vinyl Ester Product | Max. Temp. | React. Atmos. |
| --- | --- | --- | --- | --- |
| 7 | propionic acid | vinyl propionate | 130° C. | N$_2$ |
| 8 | pivalic acid | vinyl pivalate | 130° C. | N$_2$ |
| 9 | acrylic acid[1] | vinyl acrylate | 100° C. | Air |
| 10 | methacrylic acid[2] | vinyl methacrylate | 100° C. | Air |
| 11 | succinic acid | divinyl succinate | 150° C. | CO |
| 12 | terephthalic acid[3] | divinyl terephthalate | 170° C. | CO |

[1]Phenothiazine was added to the reaction mixture to inhibit polymerization.
[2]Phenothiazine was added to the reaction mixture to inhibit polymerization.
[3]The reaction was conducted in dimethyl terephthalate solvent.

EXAMPLE 13

In three batches which were later combined, ruthenium carbonyl (44.4 grams, total of the three batches), pivalic acid (510 grams, total of the three batches), and vinyl acetate (432 grams, total of the three batches) were charged to Fischer Porter bottles, flushed and pressurized (5 psig) with carbon monoxide, and heated for approximately 2 hours at 145°-160° C. This procedure resulted in a highly concentrated ruthenium catalyst solution (2.15% ruthenium or 21, 500 ppm ruthenium) which as a result of the reaction conditions, was dissolved in an equilibrated mixture of vinyl acetate, pivalic acid, vinyl pvialte, and acetic acid. When charged to the 30 gallon stainless steel reactor as described below with 10 gallons each of vinyl acetate and pivalic acid to make vinyl pivalte, a 300 ppm ruthenium catalyst concentration was achieved.

Vinyl pivalte (91 pounds) was prepared in two, 20 gallon-batch runs in a 30 gallon stainless steel reactor. In two batches, pivalic acid (75.5 lbs., 10 gallons) and vinyl acetate (77.9 lbs, 10 gallons) were transvinylated in the presence of 300 ppm ruthenium catalyst, described in the preceding paragraph, at 145° C. using a 50 psig carbon monoxide reaction atmosphere for 5 hours. Reaction product was removed from the reactor by vacuum distillation (60°-130° C., 240 mm Hg) from the ruthenium catalyst without difficulty. Based on gas chromatographic analysis, 90.4% and 94.7% of the vinyl pivalate respectively formed in the two reaction batches, could be accounted for after distillation. This demonstrates that reequilibration of vinyl pivalate (and acetic acid) to vinyl acetate (and pivalic acid) was successfully controlled during distillation within 9.6% (batch 1) and 5.3% (batch 2), respectively. Mass balances for all components were better than 98%.

EXAMPLES 14-32

Catalytic activity of numerous ruthenium precursor compounds was evaluated according to the following procedure. A mixture of the ruthenium compound, vinyl acetate (17.2 grams), benzoic acid (12.2 grams) and nonane (internal standard for gas chromatographic analysis) were charged to a Fischer-Porter bottle, sealed, purged three times with carbon monoxide and finally pressurzied to 25 psig. The magnetically-stirred reaction mixture was heated in an oil bath to the desired reaction temperature for a specified time period (both specified in the table). Gas chromatographic analysis on an DB-1 fused silica capillary column (30M) revealed the amount of vinyl benzoate formed by transvinylation (shown in the table).

| Ex. No. | Catalyst Precursor (grams) | Temp./Time °C./hr | Vinyl Benzoate (grams) |
|---|---|---|---|
| 14 | tris(aquo)-hexa-μ-oxo-triruthenium[5] heptaacetate (0.211 g) | 102/19[4] | 5.704 |
| 15 | RuCl$_3$ × H$_2$O (0.211 g) | 130/3[6] | 0.287 |
| 16 | RuCl$_3$ × H$_2$O (0.211 g) sodium acetate (1.0 g) | 130/1 | 4.072 |
| 17 | Ru$_3$(CO)$_{12}$ (0.211 g) | 130/2[7] | 6.160 |
| 18 | Ru$_3$(CO)$_{12}$ (0.21 g) | 130/2[8] | 5.025 |
| 19 | Ru$_3$(CO)$_{12}$ (0.002 g) | 130/2[9] | 1.759 |
| 20 | Ru$_3$(CO)$_{12}$ (0.021 g) | 130/2[10] | 4.722 |
| 21 | Ru$_3$(CO)$_{12}$ (0.021 g) | 130/2 | 5.027 |
| 22 | Ru$_3$(CO)$_{12}$ (0.211 g) triphenylphosphine (0.262 g) | 130/18[11] | 5.723 |
| 23 | ruthenium [5% on carbon]. (1.0 g) | 150/4 | 6.067 |
| 24 | ruthenium [5% on alumina]. (1.0 g) | 150/18 | 5.421 |
| 25 | ruthenium(III) 2,4-pentanedioate (0.06 g) | 150/4 | 5.957 |
| 26 | ruthenium powder 99.9% (0.06 g) | 150/2 | 0.126 |
| 27 | dichlorotricarbonyl-ruthenium(II) dimer (0.06 g) | 150/2 | 4.277 |
| 28 | ruthenium(IV) oxide, hydrate (0.06 g) | 150/2 | 2.762 |
| 29 | tris(2,2'-bipyridyl) ruthenium(II) chloride, hexahydrate (0.2 g) | 150/2 | NA |
| 30 | ruthenium(IV) oxide, anhydrous (0.06 g) | 150/2 | 0.045 |
| 31 | H$_4$Ru$_4$(CO)$_{12}$ (0.06 g) | 150/2 | 7.008 |
| 32 | ruthenium(III) iodide (0.06 g) | 150/2 | 0.029 |

| Ex. No. | Catalyst Precursor (grams) | Temp./Time °C./hr | Vinyl Benzoate (grams) |
|---|---|---|---|
| | (0.06 g) | | |

[4]The Fischer-Porter bottle was purged and pressurized with 25 psig nitrogen instead of 25 psig carbon monoxide.
[5]The reaction was conducted in dimethyl terephthalate solvent.
[6]See previous footnote
[7]See previous footnote.
[8]See previous footnote.
[9]See previous footnote.
[10]The Fischer-Porter bottle was purged and pressurized with 25 psig ethylene instead of 25 psig carbon monoxide.
[11]The Fischer-Porter bottle was purged and pressurized with 25 psig nitrogen instead of 25 psig carbon monoxide.

EXAMPLES 33-46

The following table demonstrates transvinylations without product isolation. In the examples recited in the table, ruthenium catalyzed transvinylations (300 ppm ruthenium) of various acidic compounds with either vinyl acetate (VA) or vinyl pivalate (VP) were conducted in a manner in which the vinyl monomer products, in lieu of isolation were characterized by GC/IR/MASS SPEC or GC retention time compared with a authentic sample. The table lists the reaction conditions.

| Ex. No. | Acidic Compound | Vinyl Source | °C./hr. | Products | Verification Technique |
|---|---|---|---|---|---|
| 33 | stearic acid | VA | 150/18 | vinyl stearate | retention |
| 34 | palmitic acid | VA | 150/5 | vinyl palmitate | GC/IR/MS |
| 35 | succinimide | VA | 150/3 | vinyl succinimide | GC/IR/MS |
| 36 | salicylic acid | VA | 160/2 | vinyl salicylate | GC/IR/MS |
| 37 | phenol | VA | 160/2 | phenyl vinyl ether | GC/IR/MS |
| 38 | 2-pyrrolidinone | VA | 180.0.5 | N-vinyl pyrrolidinone | GC/IR/MS |
| 39 | 2-pyrrolidinone | VP | 160/7[12] | N-vinyl pyrrolidinone | retention |
| 40 | etheylene glycol | VA | 150/2 | 2-methyl 1-3-dioxolane | retention |
| 41 | 2-oxazolidinone | VA | 180/1 | N-vinyl-2-oxazolidinone | GC/IR/MS |
| 42 | ethyleneurea | VA | 180/3 | N-vinyl ethyleneurea | GC/IR/MS |
| 43 | 2-hydroxyethyl-ethyleneurea | VA | 180/3 | 2-hydroxyethyl 5-vinyl ethyleneurea 1-(2-acetoxyethyl)-2-vinyloxy-imidazoline 2-acetoxyethyl-5-vinyl ethylene urea | GC/IR/MS |
| 44 | 2-hydroxyethyl acetate | VA | 115/2.5 130/2.5 150/2 | 2-vinyloxyethyl acetate | GC/IR/MS |
| 45 | 2-hydroxyethyl pivalate | VP | 150/7 | 2-vinyloxyethyl pivalate | GC/IR/MS |
| 46 | 1,1,1,3,3,3-hexafluoro-2-propanol | VP | | vinyl-(1,1,1,3,3,3-hexafluoro-2-propyl) ether | GC/IR/MS |

[12]3,000 ppm ruthenium catalyst

EXAMPLES 47-55

Using the procedure for Examples 33-46, the vinyl products recited in Examples 47-55 were made using 300 ppm of ruthenium added as ruthenium carbonyl.

Verification was not or has not yet been accomplished, but G-C product peaks are located at logical retention times for these products.

| Ex. No. | Acidic Compound | Vinyl Source | °C./hr. | Products | Verification Technique |
|---|---|---|---|---|---|
| 47 | 2,2-diphenyl acetic acid | VA | 150/6 | vinyl(2,2-diphenyl acetate) | logical retention |
| 48 | 2-benzoyl benzoic acid | VA | 150/3 | vinyl 2-benzoyl benzoate | logical retention |
| 49 | Exxon Neo Acid 913 (C₅—,C₇—,C₉— mixed neo acids) | VA | 145/3 | vinyl pivalate vinyl neoheptanoate vinyl neononanoate | logical retention |
| 50 | 1-hexanol | VP | 150/4 | hexyl vinyl ether | logical retention |
| 51 | 6-aminocaproic acid | VA | 160/4 | vinyl(N-acetyl-aminocaproate) | logical retention |
| 52 | 6-aminocaproic acid | VP | 160/7 | vinyl (N-pivoyl-aminocaproate) | logical retention |
| 53 | tri-n-propyl silanol | VP | | vinyloxy (tri-n-propyl-silane | logical retention |
| 54 | 2-hydroxyethyl acrylate | VP | | 2-vinyloxyethyl acrylate | logical retention |
| 55 | trimellitic anhydride | VP | | 5-isobenzofuran-carboxylic acid, 1,3-dihydro-1,3-dioxo-ethenyl ester | logical retention |
| 56 | o-toluenesulfonamide | VP | | N-vinyl o-toluene sulfonamide | logical retention |

EXAMPLE 57

To a Fischer-Porter bottle were charged cyclohexanecaboxylic acid (100.0 grams, 0.78 moles), vinyl acetate (134.4 grams, 1.56 moles), and ruthenium carbonyl (0.056 grams). The bottle was sealed, purged four times with carbon monoxide, and pressurized to 25 psig. The bottle was placed in a 150° C. oil bath and stirred for 4.5 hours. The resultant solution after cooling to ambient temperature, was concentrated by rotary evaporation. The residue was distilled through a vigreux column giving a fraction (53.2 grams, 54°-64° C./4/3 mm Hg) which was vinyl cyclohexane carboxylate.

EXAMPLE 58

To a Fischer Porter bottle were charged salicylic acid (13.8 grams, 100 mmoles), vinyl acetate (34.4 grams, 400 mmoles), and ruthenium carbonyl (0.03304 grams). The bottle was sealed, purged four times with carbon monoxide, and pressurized to 25 psig. The bottle was placed in an oil bath and stirred for 2 hours at a 130° C. to 140° C. The resultant solution, after cooling to ambient temperature, was concentrated by rotary evaporation. The residue was distilled through a vigreux column giving a fraction (3.81 grams, 60°-74° C./1.0 mm Hg) which was vinyl salicylate.

EXAMPLE 59

To a Fischer-Porter bottle were charged trans-cinnamic acid (148) grams, 1 mole), vinyl acetate (172 grams, 2 moles), and ruthenium carbonyl (0.201 grams). The bottle was sealed, purged three times with carbon monoxide and pressurzied to 25 psig. The bottle was placed in an oil bath and stirred for 3 hours at 145° C. The resultant solution, after cooling to ambient temperature, was concentrated by rotary evaporation. The residue was distilled through a vigreux column giving a fraction (57 grams 112°-130° C./1.0 mm Hg) which was vinyl cinnamate.

EXAMPLE 60

A mixture consisting of propionic acid (12.2 grams), vinyl acetate (17.2 grams), distilled water (0.5011 grams), nonane internal standard (0.864 grams) and ruthenium carbonyl (0.211 grams, a calculated 3,340 ppm Ru concentration) was charged to a Fischer-Porter reaction vessel, purged and pressurzied to 25 psig with nitrogen, and heated to 130° C. for 15 hours. Analysis of the cooled reaction mixture by gas chromatography indicated that the following product composition was present:

| | |
|---|---|
| vinyl acetate | 9.893 grams |
| acetic acid | 5.032 grams |
| vinyl propionate | 7.398 grams |
| propionic acid | 7.488 grams |

EXAMPLE 61

A mixture consisting of propionic acid (12.2 grams), vinyl acetate (17.2 grams,) nonane internal standard (0.8395 grams), and ruthenium carbonyl (0.021 grams, a calculated 334 ppm Ru concentration) was charged to a Fischer-Porter reaction vessel, purged and pressurized to 25 psig with nitrogen, and heated to 150° C. for 2 hours. Analysis of the reaction mixture by gas chromatography indicated that the following product composition was present:

| | |
|---|---|
| vinyl acetate | 9.759 grams |
| acetic acid | 2.811 grams |
| vinyl propionate | 8.232 grams |
| propionic acid | 5.897 grams |

EXAMPLE 62

The transvinylation of a crude vinyl acetate waste stream from an industrial plant which is contaminated with ethyl acetate, vinyl propionate, and approximatley 2% water was used to convert the contained vinyl acetate into vinyl propionate. The crude "wet" vinyl acetate (5.0 grams), propionic acid (25.0 grams), nonane standard (0.4225 grams) and ruthenium carbonyl (0.019 grams, 300 ppm Ru) were charged to a Fischer-Porter bottle, purged and pressurized to 25 psig carbon monoxide and heated 3 hours at 160° C. and sampled. The following products are tabulated:

| | |
|---|---|
| vinyl acetate | 1.227 grams |
| acetic acid | 0.654 grams |
| vinyl propionate | 1.684 grams |

EXAMPLE 63

In this example, the vinyl acetate of Example 62 was azeotropically dried prior to use. The crude vinyl acetate was dried by azeotropic refluxing on a Dean-Stark apparatus for several hours. The "anhydrous" crude vinyl acetate (5.0 grams), propionic acid (25.0 grams), nonane standard (0.4398 grams) and ruthenium carbonyl (0.019 grams, 300 ppm Ru) were charged to a Fischer-Porter bottle, purged and pressurized to 25 psig carbon monoxide and heated 3 hours at 140° C. and asmple. The following products are tabulated:

| | |
|---|---|
| vinyl acetate | 1.290 grams |
| acetic acid | 0.468 grams |
| vinyl propionate | 3.249 grams |

EXAMPLE 64

This Example illustrates the preparations of vinyl acrylate by transvinylation of vinyl neodecanoate and acrylic acid. The transvinylation reaction was carried out in a distillation kettle equipped with an addition funnel for adding acrylic acid to the kettle, a thermometer for monitoring the temperature of the reactants and a condensation column for condensing and collecting the distillate from the kettle.

The kettle was charged with 0.25 grams of $[Ru(CO)_2O_2CCH_3]_n$, 250 ml vinyl neodecanoate and 0.25 grams of phenothiazine. A total of 10 ml of acrylic acid was fed dropwise to the flask. A vacuum varying from 100 to 150 mm Hg was then drawn on the kettle and the kettle was heated to 110°-113° C. The reaction conditions were such that distillate was removed from the kettle. Acrylic acid was then fed to the kettle at a rate intended to equal the rate of distillate removal. At 112° C. and 145 mm Hg, a first fraction of distillate (fraction #1, 7 grams) was collected. The head temperature was 73°-80° C. and the pressure was 1345-150 mm Hg. Analysis of fraction #1 by capillary gas chromatography indicated that the fraction contained 84.873 area% vinyl acrylate, 8.25 area% acrylic acid, and 5,954 area% vinyl neodecanoate.

The reaction was contained for an additional three work days. On the third day, the kettle temperature was increased to 130° C. at a vacuum of 60 mm Hg. A total of 14 fractions were taken. The total weight of fractions on a daily basis are set forth below:

| | |
|---|---|
| Day 2 | 26 grams |
| Day 3 | 45 grams |
| Day 4 | 43 grams |

The purity of these fractions was generally 73-85% vinyl acrylate.

Using a procedure similar to the previous experiment except that 95 ml of acrylic acid was initially charged to the kettle, a small amount of brown polymer was observed forming in the kettle. It was found that polymerization could be prevented in the process by conditioning the catalyst prior to transvinylation. To condition the catalyst, 10 ml of acrylic acid was added to the kettle. The kettle contents were heated to 110° C. for 0.5 hours prior to heating to 130° C. Catalyst conditioning was subsequently practiced.

EXAMPLE 65

This Example illustrates the preparation of vinyl acrylate by transvinylation of vinyl neodecanoate and acrylic acid. The reactor is a scaled-up version of the reactor described in Example 64.

In this Example, 40 grams of $[Ru(CO)_2O_2CCH_3]_n$ (about 3000 ppm Ru), 7000 ml vinyl neodecanoate, and 10 grams phenothiazine were charged to the reactor. A mixture of 2700 ml acrylic acid and 10 grams of phenothiazine were charged to the addition funnel. In a dropwise manner, 280 ml of the crylic acid/phenothiazine mixture were fed to the kettle. The kettle was heated to 110° C. for 0.5 hours to condition the catalyst. After catalyst conditioning, a vacuum varying from 120-135 mm Hg was introduced and the kettle was heated to 130° C. The temperature of the reaction is such as to cause distillation of the equilibrium reaction products. The distillation condenser was cooled with a circulating low temperature bath refrigerated to less than 0° C. Acrylic acid was fed to the reactor at a rate intended to equal the rate of distillate removal. The reaction was carried out for 5 work days. At 130° C. and 130-135 mm Hg distillate fractions totalling 726 grams were collected. The head temperature was 42°-55° C.

Analysis of the combined fractions by capillary gas chromatography (GC) indicated that it contained 87.965 area% vinyl acrylate, 3.02 area% acrylic acid, and 7.694 area% vinyl neodecanoate.

On the fourth day of the reaction, the kettle temperature was about 130° C. and the vacuum ranged from 120 mm Hg to 125 mm Hg. On day 4, 346 grams of distillate was removed at 25°-63° C. Analysis of the combined fractions by capillary GC was not conducted, however all fractions from this experiment were combined and analyzed, and later fractionally distilled under vacuum on a 10-tray Oldershaw column. GC analysis of the combined fractions charged to the kettle revealed: 87.796 area% vinyl acrylate, 4.382 area% acrylic acid, and 5.854 area% vinyl neodecanoate.

The combined fractions from this experiment were charged to a distillation kettle eqiupped with a 10-tray Oldershaw column, a fractionating head, and an addition funnel through which an inhibiting solution of phenothyiazine in vinyl acrylate could be fed continuously to the top of the column. Vinyl acrylate was fractionated at a reduced pressure of 115-125 mm Hg at 34°-43° C. (typically 38°-40° C.) A total of 848 grams of product was distilled. The purity was 99+%.

EXAMPLE 66

This Example illustrates the preparation of vinyl acrylate by transvinylation of vinyl-2-ethylhexanoate with acrylic acid. The apparatus is the same as that described in Example 64.

In this Example, 0.1064 grams of $[Ru(CO)_2O_2CCH_3]_n$ (1000 ppm Ru) and 50 grams of vinyl-2-ethylhexanoate were charged to the reaction kettle. A mixture of 15 grams acrylic acid and 0.05 grams phenothiazine was charged to a 50 ml addition funnel. About 3 to 5 ml of acrylic acid was then added to the kettle before conditioning. THe kettle was then heated to 110° C. with a 200 mm Hg vacuum for 1 hour to condition the catalyst mixture against polymerization. After catalyst conditioning, the kettle temperature was increased to 130°-140° C. The reaction temperature is sufficient that distillate is removed from the reaction kettle. The acrylic acid/phenothiazine solution was then fed to the reaction kettle dropwise at a rate equal to the rate of distillate removal overhead. A first fraction of distillate, about 1 gram, was collected at 49° C. with a vacuum of 195 mm Hg. Analysis of fraction #1 by cpaillary gas chromatography (GC) indicated that there was 77.73 area% of vinyl acrylate, 7.43 area% of acrylic acid and 13.98 area% of vinyl-2-ethylhexanoate. A second fraction of distillate, about 4 grams, and a third fraction, about 6 grams, were collected at 49°-89° C. with a 280 mm Hg vacuum. Analysis of fraction #2 and #3 by capillary GC indicated that there were 71.47 area% and 68.81 area % of vinyl acrylate respectively.

EXAMPLE 67

This Example illustrates the preparation of vinyl methacrylate by transvinylation of vinyl neodecanoate and methacrylic acid. The reaciton was conducted in a kettle equipped in the same manner as the kettle in Example 64, except that a Vigreux column was substituted for the condensing column.

In this Example, 15 grams $[Ru(CO)_2O_2CCH_3]_n$ (about 1000 ppm Ru), 7000 ml vinyl neodecanoate and 10 grams phenothiazine were charged to the reaction kettle. A mixture of about 1 gallon methacrylic acid and 10 grams of phenothiazine was charged to the addition funnel. In a dropwise manner, 280 ml of methacrylic acid was fed to the reactor and the kettle was heated to 110° C. for 1 hour to condition the catalyst. A vacuum varying from 90-100 mm Hg was introduced and the kettle was heated to 130° C. The distillation condenser was cooled with a ciruclating low temperature bath refrigerated to less than 0° C. The methacrylic acid-phenothiazine mixture was then fed to the reactor at a rate intended to equal the rate of distillate removal. Five (5) fractions were collected. The reaction conditions of each fraction and the analysis of fractions 1, 2 and 3 by capillary gas chromatography (GC) are set forth in the followint able:

| Fraction # (grams) | Pressure mm Hg | Head Temp °C. | % vinyl methacrylate | % methacrylic acid | % vinyl neodecanoate |
|---|---|---|---|---|---|
| 1 (548) | 100-120 90-100 | 41-53° 45-75° | 85.213 | 1.146 | 12.783 |
| 2 (825) | 145-175 100-140 75-100 | 60-61° 47-65° 42-61° | 89.5.369 | 1.303 | 3.053 |
| 3 (564) | 80-95 | 45-61° | 81.121 | 3.318 | 14.138 |
| 4 (1062) | 75-90 | 45-60° | | | |
| 5 (507) | 60-100 | 31-57° | | | |

Fractions 4 and 5 were not analyzed by capillary GC. However, all fractions collected were combined and analyzed subsequently. Analysis by capillary gas chromatography of the combined fractions revealed: 86.941 area% vinyl methacrylate, 4.896 area% methacrylic acid, and 7.910 area% vinyl neodecanoate.

The combined fractions were charged to a distillation kettle equipped with a 10-tray Olershaw colukn, a fractionating head, and an addition funnel through which an inhibiting solution of phenothiazine in vinyl methacrylate could be fed continuously to the top of the column. Vinyl methacrylate was fractionated from the combined fractions at a reduced pressure of 120-140 mm Hg at 59°-63° C. A total of 3,108 grams of product was distilled. The purity was 99+% vinyl methacrylate.

EXAMPLE 68

This Example illustrates the preparation of vinyl methacrylate by tranvinylation of vinyl stearate with methacrylic acid. The reaction was carried out in a reactor equipped in the manner of the reactor described in Example 64.

In this Example, 0.1064 grams of $[Ru(CO)_2O_2CCH_3]_n$ (1000 ppm Ru) and 50 grams of vinyl stearate were charged to the reactor. A mixture of 15 grams methacrylic acid and 0.05 gram phenothiazine was charged to the addition funnel. About 3-5 ml of the methacrylic acid/phenothiazine mixture was added to the kettle. The reaction kettle was heated to 110° C. with a 200 mm Hg vacuum for 1 hour to condition the catalyst against polymerization. After conditioning, dropwise at a rate equal to the rate of distillate removal overhead. One 10-gram fraction was collected between 82°-98° C. with a 135-220 mm Hg vacuum. Analysis of the distillate by capillary gas chromatography indicated tha there was 74.13 area% of vinyl methacrylate and 24.5 area% of methacrylic acid.

I claim:

1. A process for the preparation of a vinyl derivative of a thermally labile Bronsted acid by transvinylation comprising reacting in a reactor a vinyl derivative of a first Bronsted acid with a thermally labile Bronsted acid in the presence of a catalyst, said catalyst comprising a ruthenium compound capable of catalyzing the transvinylation reaction, said vinyl derivative of said first Bronsted acid having a boiling point in the range of from about equal to the boiling point of said thermally labile Bronsted acid to greater than the boiling point of the thermally labile Bronsted acid and higher than the boiling point of the vinyl derivative of the thermally labile Bronsted acid, feeding said thermally labile Bronsted acid to the reactor during transvinylation at a rate to maintain the concentration of thermally labile Bronsted acid in the reactor at less than about 40 mole %, and removing said vinyl derivative of the thermally labile Bronsted acid from the reactor as the transvinylation reaction progresses.

2. THe process of claim 1 wherein said vinyl derivative of the thermally liable Bronsted acid is thermally liable and the combiend concentration of thermally labile Bronsted acid and vinyl derivative of said thermally labile Bronsted acid is maintained at leass than about 40 mole %.

3. The process of claim 2 wherein the combined concentration of the thermally labile Bronsted acid and said vinyl derivative of the thermally labile Bronsted acid is maintained at less than about 20 mole %.

4. The process of claim 1 wherein the thermally labile Bronsted acid is fed to the reactor at a rate to maintain the concentration of thermally labile acid in the range of from about 5 to about 25 mole %.

5. The process of claim 1 wherein sai thermally labile Bronsted acid is a compound of the formula

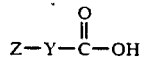

wherein Z has the formula

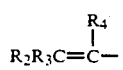

and Y is $(CH_2)_n$, aryl or substituted aryl, $R_2$, $R_3$ and $R_4$ are each individually one of hydrogen, alkyl, aryl, halo, cyano, carbonyl, keto or carboxylate, and wherein where Y is $(CH_1)_n$, n is zero or one.

6. The process of claim 1 wherein said thermally labile Bronsted acid is a hydroxyl derivative of benzoic acid.

7. The process of claim 1 wherein said vinyl derivative of said first Bronsted acid has a boiling point at least about 20° C. higher than the boiling point of said thermally labile Bronsted acid.

8. The process of claim 1 wherein said vinyl derivative of said first Bronsted acid has a boiling point at least about 50° C. higher than the boiling point of said thermally labile Bronsted acid.

9. The process of claim 2 wherein said vinyl derivative of said first Bronsted acid has a boiling point at least about 20° C. higher than the boiling point of said thermally labile Bronsted acid.

10. The process of claim 2 wherein said vinyl derivative of said first Bronsted acid has a boiling point at least about 50° C. higher than the boiling point of said thermally labile Bronsted acid.

11. The process of claim 2 wherein said thermally labile Bronsted acid is a compound of the formula

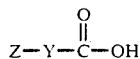

wherein Z has the formula:

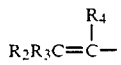

and Y is $(CH_2)_n$, aryl or substituted aryl, $R_2$, $R_3$ and $R_4$ are each individually one of hydrogen, alkyl, aryl, halo, cyano, carbonyl, keto or carboxylate, and wherein where Y is $(CH_2)_n$, n is zero or one.

12. The process of cliam 2 wherein said thermally labile Bronsted acid is a hydroxyl derivative of benzoic acid.

13. The process of claim 11 wherein said vinyl derivative of said first Bronsted acid has a boiling point at least about 20° C. higher than the boiling point of said thermally labile Bronsted acid.

14. The process of claim 11 wherein said vinyl derivative of said first Bronsted acid has a boiling point at least about 50° C. higher than the boiling point of said thermally labile Bronsted acid.

15. The process of claim 1 wherein said catalyst is a ruthenium compound selected from the group consisting of ruthenium carbonyl, ruthenium carboxylate and ruthenium carbonyl carboxylate compounds.

16. The process of claim 2 wherein said catalyst is a ruthenium compound selected from the group consisting of ruthenium carbonyl, ruthenium carboxylate and ruthenium carbonyl carboxylate compounds.

17. The process of claim 5 wherein said catalyst is a ruthenium compound selected from the group consisting of ruthenium carbonyl, ruthenium carboxylate and ruthenium carbonyl carboxylate compounds.

18. The process of claim 6 wherein said catalyst is a ruthenium compound selected from the group consisting of ruthenium carbonyl, ruthenium carboxylate and ruthenium carbonyl carboxylate compounds.

19. The process of claim 11 wherein said catalyst is a ruthenium compound selected from the group consisting of ruthenium carbonyl, ruthenium carboxylate and ruthenium carbonyl carboxylate compounds.

20. The process of claim 12 wherein said catalyst is a ruthenium compound selected from the group consisting of ruthenium carbonyl, ruthenium carboxylate and ruthenium carbonyl carboxylate compounds.

21. The process of claim 13 wherein said catalyst is a ruthenium compound selected from the group consisting of ruthenium carbonyl, ruthenium carboxylate and ruthenium carbonyl carboxylate compounds.

22. The process of claim 14 wherein said catalyst is a ruthenium compound selected from the group consisting of ruthenium carbonyl, ruthenium carboxylate and ruthenium carbonyl carboxylate compounds.

23. The process of claim 1 wherein the process is carried out at a temperature of from about 80° C. to about 160° C.

24. The process of claim 1 wherein the process is carried out at a temperature of from about 110° C. to about 140° C.

25. The process of claim 5 wherein the process is carried out at a temperature of from about 80° C. to about 160° C.

26. The process of claim 5 wherein the process is carried out at a temperature of from about 110° C. to about 140° C.

27. The process of claim 6 wherein the process is carried out at a temperature of from about 80° C. to about 160° C.

28. The process of claim 6 wherein the process is carried out at a temperature of from about 110° C. to about 140° C.

29. The process of claim 16 wherein the process is carried out at a temperature of from about 80° C. to about 160° C.

30. The process of claim 16 wherein the process is carried out at a temperature of from about 110° C. to about 140° C.

31. The process of claim 17 wherein the process is carried out at a temperature of from about 80° C. to about 160° C.

32. The process of claim 17 wherein the process is carried out at a temperature of from about 110° C. to about 140° C.

33. The process of claim 19 wherein the process is carried out at a temperature of from about 80° C. to about 160° C.

34. The process of claim 19 wherein the process is carried out at a temperature of from about 110° C. to about 140° C.

35. The process of claim 20 wherein the process is carried out at a temperature of from about 80° C. to about 160° C.

36. The process of claim 20 wherein the process is carried out at a temperature of from about 110° C. to about 140° C.

37. The process of claim 27 wherein said vinyl derivative of said first Bronsted acid is a vinyl ester of a carboxylic acid.

38. The process of claim 29 wherein said vinyl derivative of said first Bronsted acid is a vinyl ester of a carboxylic acid.

39. The process of claim 33 wherein said vinyl derivative of said first Bronsted acid is a vinyl ester of a carboxylic acid.

40. The process of claim 37 wherein said thermally labile Bronsted acid is acrylic acid.

41. The process of claim 38 wherein said thermally labile Bronsted acid is acrylic acid.

42. The process of claim 39 wherein said thermally labile Bronsted acid is acrylic acid.

43. The process of claim 37 wherein said thermally labile Bronsted acid is methacrylic acid.

44. The process of claim 38 wherein said thermally labile Bronsted acid is methacrylic acid.

45. The process of claim 39 wherein said thermally labile Bronsted acid is methacrylic acid.

46. The process of claim 40 wherein said vinyl ester of said carboxylic acid is selected from the group consisting of vinyl pivalte, vinyl valerate, vinyl neodecanoate, vinyl 2-ethylhexanoate, vinyl neononanoate, vinyl benzoate, vinyl hpetanoate, vinyl laurate, vinyl palmitate, vinyl stearate and vinyl versatate.

47. The process of claim 41 wherein said carboxylic acid is selected from the group consisting of vinyl pivalate, vinyl valerate, vinyl neodecanoate, vinyl 2-ethylhexanoate, vinyl neononanoate, vinyl benzoate, vinyl heptanoate, vinyl laurate, vinyl palmitate, vinyl stearate and vinyl versatate.

48. The process of claim 42 wherein said carboxylic acid is selected from the group consisting of vinyl pivalate, vinyl valerate, vinyl neodecanoate, vinyl 2-ethylhexanoate, vinyl neononanoate, vinyl benzoate, vinyl heptanoate, vinyl laurate, vinyl palmitate, vinyl stearate and vinyl versatate.

49. The process of claim 43 wherein said carboxylic acid is selected from the group consisting of vinyl pivalate, vinyl valerate, vinyl neodecanoate, vinyl 2-ethylhexanoate, vinyl neononanoate, vinyl benzoate, vinyl heptanoate, vinyl laurate, vinyl palmitate, vinyl stearate and vinyl versatate.

50. The process of claim 44 wherein said vinyl ester of said carboxylic acid is selected from the group consisting of vinyl pvialate, vinyl valerate, vinyl neodecanoate, vinyl 2-ethylhexanoate, vinyl neononanoate, vinyl benzoate, vinyl heptanoate, vinyl laurate, vinyl palmitate, vinyl stearate and vinyl versatate.

51. The process of claim 46 wherein said vinyl ester of said carboxyclic acid is selected from the group consisting of vinyl pvialate, vinyl valerate, vinyl neodecanoate, vinyl 2-ethylhexanoate, vinyl neononanoate, vinyl benzoate, vinyl heptanoate, vinyl laurate, vinyl palmitate, vinyl stearate and vinyl versatate.

52. The process of claim 37 wherein said vinyl ester of said carboxylic acid is a polymer which contains vinyl derivatives of carboxylic acids.

53. The process of claim 38 wherein said vinyl ester of said carboxylic acid is a polymer which contains vinyl derivatives of carboxylic acids.

54. The process of claim 39 wherein said vinyl ester of said carboxylic acid is a polymer which contains vinyl derivatives of carboxylic acids.

* * * * *

UNITED STATES PATENT AND TRADEMARK OFFICE
CERTIFICATE OF CORRECTION

PATENT NO. : 5,155,253

DATED : October 13, 1992

INVENTOR(S) : Rex Murray

It is certified that error appears in the above-identified patent and that said Letters Patent is hereby corrected as shown below:

Column 1, lines 15 thru 20 "a vinyl derivative of a Bronsted acid with a different Bronsted acid which comprises providing a liquid phas a vinyl derivative of a Bronsted acid with a different Bronsted acid which comprises providing a liquid phase" should read --a vinyl derivative of a Bronsted acid with a different Bronsted acid which comprises providing a liquid phase--

Column 1, line 54 "Adlman" should read --Adelman--

Column 1, line 61 "yield" should read --yields--

Column 1, line 66 "mor" should read --more--

Column 2, line 51 "sytem" should read --system--

Column 2, line 57 "Roten," should read --Rotem,--

Column 2, line 67 "stidued" should read --studied--

Column 2, line 67 "ruthernium" should read --ruthenium--

Column 3, line 63 "reaction" should read --reactor--

Column 3, line 64 "theramlly" should read --thermally--

Column 4, line 11 "DETAILES" should read --DETAILS--

Column 5, line 13 "sulfanamide;" should read --sulfonamide;--

Column 6, line 29 "aic,d" should read --acid,--

Column 6, line 44 "acidhas" should read --acid has --

UNITED STATES PATENT AND TRADEMARK OFFICE
CERTIFICATE OF CORRECTION

PATENT NO. : 5,155,253

DATED : October 13, 1992

INVENTOR(S) : Rex Murray

It is certified that error appears in the above-identified patent and that said Letters Patent is hereby corrected as shown below:

Column 7, line 30 "tehrmal" should read --thermal--

Column 8, line 17 "anhdride" should read --anhydride--

Column 8, line 24 "product" should read --produce--

Column 8, line 44 "erduced" should read --reduced--

Column 9, line 1 "slightly" should read --slight--

Column 9, line 15 "responsibel" should read --responsible--

Column 9, line 18 "condntions," should read --conditions,--

Column 10, line 60 "acide." should read --acid.--

Column 12, line 45 "vacuu," should read --vacuum,--

Column 13, line 29 "15;" should read --15--

Column 13, line 37 "hexa-$\mu$-aceto-$\mu_3$-oxo-triruthenium" should read --hexa-$\mu$-aceto-$\mu_3$-triruthenium--

Column 14, line 7 "hexa-$\mu$-aceto-$\mu_3$-oxo-triruthenium" should read --hexa-$\mu$-aceto-$\mu_3$-oxo-triruthenium--

Column 14, line 17 "70.5° C.)." should read --80.5° C.).--

Column 14, line 31 "followint" should read --following--

Column 14, line 58 "(5 psig) should read --(25 psig)--

Column 14, line 67 "pivalte," should read --pivalate--

UNITED STATES PATENT AND TRADEMARK OFFICE
CERTIFICATE OF CORRECTION

PATENT NO. : 5,155,253

DATED : October 13, 1992

INVENTOR(S) : Rex Murray

It is certified that error appears in the above-identified patent and that said Letters Patent is hereby corrected as shown below:

Column 15, line 1 "pivalte" should read --pivalate--

Column 18, line 50 "approximatley" should read --approximately--

Column 19, line 8 "asmple" should read --sample--

Column 19, line 40 "5,954" should read --5.954--

Column 19, line 44 "60 mm Hg" should read --160 mm Hg--

Column 20, line 8 "crylic" should read --acrylic--

Column 20, line 41 "phenothyiazine" should read --phenothiazine--

Column 20, line 58 "THe" should read --The--

Column 20, line 68 "cpaillary" should read --capillary--

Column 21, line 13 "reaciton" should read --reaction--

Column 21, line 27 "ciruclating" should read --circulating--

Column 21, line 34 "followint" should read --following--

Column 21, line 56 "Olershaw colukn" should read --Oldershaw column--

Column 22, line 12 "After conditioning, dropwise at rate equal" should read --After conditioning, the kettle temperature was increased to 130-140°C. The reaction conditions were such that distillate was removed from the Kettle. The methacrylic acid/ phenothiazine solution was then fed to the reactor dropwise at a rate equal to the rate of distillate removal overhead.--

UNITED STATES PATENT AND TRADEMARK OFFICE
CERTIFICATE OF CORRECTION

PATENT NO. : 5,155,253

DATED : October 13, 1992

INVENTOR(S) : Rex Murray

It is certified that error appears in the above-identified patent and that said Letters Patent is hereby corrected as shown below:

Column 22, line 40 "THe" should read --The--

Column 22, line 42 "combiend" should read --combined--

Column 22, line 44 "lease" should read ----less--

Column 22, line 54 "sai" should read --said--

Column 23, line 2 "$(CH_1)_n,$" should read --$(CH_2)_n,$--

Column 25, line 14 "pivalte," should read --pivalate--

Column 25, line 16 "hpetanoate," should read --heptanoate,--

Column 26, line 9 "pvialate," should read --pivalate,--

Column 26, line 16 "pvialate," should read --pivalate,--

Signed and Sealed this

Eleventh Day of October, 1994

Attest:

BRUCE LEHMAN

Attesting Officer     Commissioner of Patents and Trademarks